United States Patent

Nakamura et al.

[11] Patent Number: 5,919,398
[45] Date of Patent: Jul. 6, 1999

[54] OIL-WATER MIXED COMPOSITION

[75] Inventors: Fumiaki Nakamura; Koji Abe; Kenzo Ito, all of Yokohama, Japan

[73] Assignee: Shiseido Co., Ltd., Tokyo, Japan

[21] Appl. No.: 08/750,015

[22] PCT Filed: Mar. 10, 1996

[86] PCT No.: PCT/JP96/00842

§ 371 Date: Apr. 16, 1997

§ 102(e) Date: Apr. 16, 1997

[87] PCT Pub. No.: WO96/29975

PCT Pub. Date: Oct. 3, 1996

[30] Foreign Application Priority Data

Mar. 31, 1995 [JP] Japan ................................. 7-100548
Mar. 31, 1995 [JP] Japan ................................. 7-100549
May 26, 1995 [JP] Japan ................................. 7-152404
May 26, 1995 [JP] Japan ................................. 7-152405

[51] Int. Cl.$^6$ .............................. A61K 7/00; A61K 9/10; B01J 13/00
[52] U.S. Cl. ...................... 252/315.4; 424/401; 514/873; 514/944; 516/104; 516/108
[58] Field of Search ............................ 252/315.1, 315.3, 252/315.4, 315.6; 424/401; 514/873, 944

[56] References Cited

U.S. PATENT DOCUMENTS 4,772,592  9/1988  Benzoni ..................................... 514/63
4,780,145  10/1988  Mori et al. ............................... 106/206
5,061,481  10/1991  Suzuki et al. ............................. 424/63
5,362,482  11/1994  Yoneyama et al. ........................ 424/69

FOREIGN PATENT DOCUMENTS 56-104807  8/1981  Japan .
56-150007  11/1981  Japan .
57-16812  1/1982  Japan .
57-38936  3/1982  Japan .
57-62214  4/1982  Japan .
58-124535  7/1983  Japan .
61-66752  9/1984  Japan .

Primary Examiner—Richard D. Lovering
Attorney, Agent, or Firm—Ronald R. Snider

[57] ABSTRACT

An oil-water mixed composition is consisted of a solid or semisolid oil phase at room temperature, and a water phase which is dispersed into the oil phase. The water phase contains a humectant and is solid or semisolid at room temperature. Preferably, the oil phase contains hydrophobic silica, dextrin fatty acid ester or polyvalent alcohol oligo ester of long chain monocarboxylic acid and long chain dicarboxylic acid.

The oil-water mixed composition is superior in stability with passage of time and safety. In addition, this composition has demonstrated little stickiness and sensation of unsuitability for skin, and has much emollient effect (i.e., to prevent the skin from dryness) and is persistent in preserving its emollient effect.

27 Claims, No Drawings

OIL-WATER MIXED COMPOSITION

This application is a 371 of PCT/JP96/00842 filed Mar. 10, 1996.

TECHNICAL FIELD

This invention relates to an oil-water mixed composition, and in particular, relates to an improvement of oil- water mixed mechanism of the composition.

BACKGROUND ART

Some cosmetics and drugs have a formulation of an oil-in-water or a water-in-oil emulsion mainly composed of a water phase and an oil phase component such as milky lotion, cream or ointment.

Conventionally, a surfactant is required in order to manufacture such an oil-in-water or water-in-oil emulsion.

However, a surfactant used in conventional cosmetic treatment often causes skin irritation, so not a few consumers feel misgivings. In addition, an oil-in-water or water-in-oil emulsion containing a surfactant is often criticized as being unstable with passage of time, sticky, and poor in water resistance.

Under these circumstances, several emulsions containing little or no surfactant have recently been developed.

For example, instead of using a surfactant, it is known the emulsion which uses clay mineral (Japanese Unexamined Patent Publication No.56-150007, No.57-16812, No.58-124535 and Japanese Patent Publication No.64-3529), silicone oil (Japanese Unexamined Patent Publication No.61-66752), glycyrrhizin Japanese Unexamined Patent Publication No57-62214), and the like as emulsifier or assistant emulsifier.

Nevertheless, the emulsions shown above do not appear to have improved the stability of the emulsions with passage of time, and, it is too early to speculate at this time that the emulsions shown above have solved the problems relating to skin irritation, stickiness and water resistance.

DISCLOSURE OF INVENTION

In view of the foregoing problems of the prior art, the objective of this invention is to provide an oil- water mixed composition which is superior in stability and safety, without relying upon the use of a high amount of surfactant.

As a result of diligent studies of the inventors to attain the above-mentioned object, it has been found that an oil-water mixed composition which has excellent stability without a surfactant can be acquired by dispersing a water phase into solid or semisolid oil phase uniformly at room temperature, and thus this invention has been accomplished.

Namely, in embodiment 1 an oil-water mixed composition in accordance with the present invention is characterized in that it contains a solid or semisolid oil phase at room temperature, and a water phase dispersed into said oil phase at room temperature.

Preferably, the water phase contains a humectant and is solid or semisolid at room temperature.

Preferably, the oil phase contains an oil component which makes the oil phase solid or semisolid at room temperature constitutes 10 to 70% by weight with respect to the whole amount of the oil-water mixed composition.

Also preferably, the humectant in the water phase constitutes 10 to 70% by weight with respect to the whole amount of the oil-water mixed composition.

Preferably, the oil-water mixed composition does not contain a surfactant practically.

In embodiment 2, the oil phase contains a hydrophobic silica and is solid or semisolid.

Also preferably, the oil phase forms a continuous phase.

Preferably, the hydrophobic silica constitutes 0.1 to 10% by weight with respect to the whole amount of the oil-water mixed composition.

Preferably, the oil phase contains an oil component which makes the oil phase solid or semisolid at room temperature constitutes 1 to 70% by weight with respect to the whole amount of the oil-water mixed composition.

Preferably, the water phase contains a humectant and the humectant constitutes 1 to 70% by weight with respect to the whole amount of the oil-water mixed composition.

Preferably, the oil-water mixed composition does not contain a surfactant practically.

In embodiment 3, the oil phase contains a dextrin fatty acid ester and is solid or semisolid.

Also preferably, the oil phase forms a continuous phase.

Preferably, a dextrin fatty acid ester constitutes 0.1 to 10% by weight with respect to the whole amount of the oil- water mixed composition.

Preferably, the oil phase contains an oil component which makes the oil phase solid or semisolid at room temperature, wherein said solid or semisolid oil component constitutes 1 to 70% by weight with respect to the whole amount of the oil-water mixed composition.

Preferably, the water phase contains a humectant and the humectant constitutes 1 to 70% by weight with respect to the whole amount of the oil-water mixed composition.

Also preferably, the oil-water mixed composition does not contain a surfactant practically.

In embodiment 4, the oil phase contains a polyvalent alcohol oligo ester of long chain monocarboxylic acid and long chain dicarboxylic acid and is solid or semisolid.

Also preferably, the oil phase forms a continuous phase.

Preferably, such a polyvalent alcohol oligo ester is acquired by the esterification of the following (a), (b) and (c):
(a) one or more selected from the group of glycerin, glycerin condensate, trimethylolethane, trimethylolpropane and pentaerythritol;
(b) one or more selected from the group consisting of straight chain fatty acid, branched chain fatty acid, unsaturated fatty acid and hydroxy fatty acid having a carbon number of 12 to 22;
(c) one or more selected from the group of dibasic acid which has straight or branched chain having a carbon number of 12 to 22.

Preferably, the polyvalent alcohol oligo ester is glycerin behenate eicosan dicarboxylic ester.

Preferably, the polyvalent alcohol oligo ester constitutes 0.1 to 10% by weight with respect to the whole amount of the oil-water mixed composition.

Preferably, the polyvalent alcohol oligo ester constitutes 0.1 to 10% by weight with respect to the whole amount of the oil-water mixed composition.

Also preferably, the oil phase contains an oil component which makes the oil phase solid or semisolid at room temperature constitutes 1 to 70% by weight with respect to the whole amount of the oil-water mixed composition.

Preferably, the water phase contains a humectant and the humectant constitutes 1 to 70% by weight with respect to the whole amount of the oil-water mixed composition.

Preferably, the oil-water mixed composition does not contain a surfactant practically.

Further, the expression "solid or semisolid" as used herein means the conditions that can maintain the same configuration in the case of leaving an oil phase, a water phase or a composition under the room temperature.

BEST MODE FOR CARRYING OUT THE INVENTION

The preferred embodiments of this invention are shown as follows:

In order to disperse a water phase into a semisolid or solid oil phase uniformly at room temperature, the following four ways are recommended:
1. Adding a humectant into a water phase to make it solid or semisolid at room temperature.
2. Adding a hydrophobic silica into a solid or semisolid oil phase at room temperature.
3. Adding a dextrin fatty acid ester into a solid or semisolid oil phase at room temperature.
4. Adding a polyvalent alcohol oligo ester consisting of long chain monocarboxylic acid and long chain dicarboxylic acid into a solid or semisolid oil phase at room temperature.

In the circumstances of adopting the above four ways, when manufacturing an oil-water mixed composition, a solid or semisolid oil phase and a water phase are dispersed uniformly and stabilized.

Next, the results from the use of the above four ways are shown as follows:

Embodiment 1

Adding a humectant into a water phase to make it solid or semisolid at room temperature.

In this embodiment, both of the oil phase and the water phase are "solid or semisolid at room temperature".

The experiments are carried out by dissolving the oil phase and the water phase, separately and uniformly, under heat. After adding the dissolved water phase to the oil phase, the two phases are mixed together under constant stirring and gradually cooled down. The results of this procedure produce "a solid or semisolid oil-water mixed composition at room temperature" with the oil phase and water phase dispersed uniformly.

A solid or semisolid oil component used to make the oil phase solid or semisolid at room temperature is selected from a group comprising wax esters (e.g. microcrystalline wax, beeswax), solid paraffin, hydrogenated oil, tallow, Japan wax, beeswax, candelilla wax, carnauba wax, ceresin, vaseline, lanolin, lanolin derivatives, cholesterol, cholesterol derivatives and the like. Among these oil component, microcrystalline wax or vaseline are especially preferable in view of the effect. Although the amount of the compounding of these solid or semisolid oil component relates to another oil phase component, the amount is essential in making the oil phase solid or semisolid. Preferably, the amount of this oil component is made of 10 to 70% by weight and more preferably 10 to 40% by weight with respect to the whole amount of the oil-water mixed composition. If the amount of this oil component is less than 10% by weight, the composition would be unstable at high temperature. If the amount of this oil component is more than 70% by weight, the oil-water mixed composition would be too rigid and difficult to use.

The humectant which is added in the water phase to make the water phase solid or semisolid is selected from a group consisting of polyethylene glycol, sorbitol, maltitol, hyaluronic acid, chondroitin sulfate, erythritol, trimethyl glycin, sodium lactate, pyrrolidonecarboxylic acid and the like. Polyethylene glycol is the most preferable humectant in view of the effect.

Although the amount of the compounding of these humectants relates to another water phase component, the amount is essential in making the oil phase solid or semisolid. Preferably, the amount of the humectant is composed 10 to 70% by weight and more preferably 10 to 40% by weight with respect to the whole amount of the oil-water mixed composition. If the amount of humectant is less than 10% by weight, the oil-water mixed composition would be unstable. If the humectant exceeds 70% by weight, the oil-water mixed composition would be too rigid and difficult to use.

Some ingredients, which are commonly used in external preparation of cosmetics or drugs, can also be added to the oil-water mixed composition without directly spoiling the desired effect of this invention.

These ingredients include powder components (e.g., titanium dioxide, mica, talc, silk powder, nylon powder, cellulose powder, silicone powder, polytetrafluoroethylene powder, hydrophobic treated powder and the like), hydro carbon (e.g., liquid paraffin, squalane and the like), extra oil from animals or plants tissue (e.g., olive oil, macadamia nut oil, tsubaki oil, jojoba oil, liquid lanolin and the like), and liquid oil components (e.g., silicone oil, perfluoro oil, fatty acid, higher alcohol, ester oils and the like which is obtained from the reaction thereof and the like which re obtained from the reaction thereof and the like).

There are also other ingredients that can be added to the oil-water mixed composition. These include liquid humectants (e.g., propylene glycol, dipropylene glycol, 1,3-butylene glycol, glycerin, diglycerine, lactic acid and the like), antiseptics (e.g., ester parahydroxybenzoate, benzoic acid, sodium benzoate, sorbic acid, potassium sorbate, phenoxyethanol and the like), ultraviolet absorbers (e.g., p-aminobenzoic acid, homomenthyl-7N-acetyl anthranilate, butyl methoxy benzoylmethane, glyceryl di-p-methoxy cinnamate, amyl salicylate, octyl methoxycinnamate, 2,4-dihydroxy-benzophenone and the like), vitamin A and its derivatives, vitamin B (e.g., vitamin $B_6$ hydrochloride, vitamin $B_6$ tripalmitate, vitamin $B_6$, dioctanoate, vitamin $B_2$ and its derivatives, vitamin $B_{12}$, vitamin $B_{15}$ and its derivatives and the like), vitamin C (e.g., ascorbic acid, ascorbyl sulfate [salt], ascorbyl phosphate [salt], ascorbyl dipalmitate, ascorbyl glucoside and the like), vitamin E (e.g., α-tocopherol, β-tocopherol, γ-tocopherol, vitamin E acetate, vitamin E nicotinate and the like), vitamin D, vitamin H and others such as pantothenic acid, pantethine, nicotin amide, benzyl nicotinate, γ-oryzanol, allantoin, glycyrrhizinic acid [salt], glycyrrhezinic acid and its derivatives, hinokitiol, rumex japonicus hout, bisabolol, eucalyptol, thymol, inositol, saponins (e.g., saiko saponin, ginseng saponin, sponge cucumber gourd saponin, mukurossi saponin, pantothenyl ethyl ether, ethynylestradiol, tranexamic acid, cephalanthin, placental extract, pigments, sequestering agents, antioxidants, fragrances, film formers and the like.

Although the oil-water mixed composition described in this invention does not require the addition of a surfactant, adding a small quantity of surfactant can improve the stability of the composition without jeopardizing its usability and stability.

Also the oil-water mixed composition in this invention shows superior effects in stability, safety and as an emollient (i.e., to prevent the skin from dryness), and is long-lasting, as compared to other existing oil-water mixed emulsions.

This newly invented oil-water mixed composition can be used in cosmetics drugs and quasi-drugs, and can be applied to epidermis and hair.

The test results of this embodiment are shown in Table 1 and 2.

The manufacturing process of each test sample is described as follows:

The water phase and the oil phase are respectively heated at 80° C. until complete dissolution. Then, the completely dissolved water phase is uniformly dispersed into the completely dissolved oil phase using a homodisperser in high speed. The mixture is allowed to cool down to 40° C. under constant stirring.

To test the stability, each sample is evaluated by the changes of color tone, smells, external appearance and sensation of use after storage at −15° C., 0° C., 5° C., 30° C. and 45° C. for three months.

○: No change in color tone, smells, external appearance and sensation of use.

X: Some change in color tone, smells, external appearance and sensation of use.

As demonstrated in Table 1, the oil-water mixed composition is less stable when its oil phase in liquid form, regardless of whether its water phase is solid or semisolid. However, when the oil phase is semisolid or solid, the stability of the oil-water mixed composition is much enhanced if the water phase is in solid form.

Also as shown in Table 2, the oil-water mixed composition is less stable when its water phase is in liquid form, regardless of whether its oil phase is solid or semisolid. However, when the water phase is semisolid or solid, the stability of the oil-water mixed composition is much enhanced when its oil phase and water phase are both in semisolid or solid form.

As a results of foregoing, excellent stability was observed when its oil phase and water phase are both in semisolid or solid form.

Furthermore, inventors have manufactured the various oil-water mixed composition and studied the stability and the usability of these compositions.

The methods of manufacturing of various mixed compositions and evaluating of the stability are described above.

After applying these samples to 30 women, evaluating the stickiness, unsuitability for skin, emollient effect, and persistence of emollient effect under the following standard;

TABLE 1

| | Test examples | | | | | | | | |
|---|---|---|---|---|---|---|---|---|---|
| | 1-1 | 1-2 | 1-3 | 1-4 | 1-5 | 1-6 | 1-7 | 1-8 | 1-9 |
| Oil phase (60%) | | | | | | | | | |
| liquid paraffin | 60 | 50 | 40 | 30 | 20 | 10 | 5 | 1 | 0 |
| microcrystalline wax | 0 | 10 | 20 | 30 | 40 | 50 | 55 | 59 | 60 |
| Properties of oil phase | liquid | liquid | semi-solid | semi-solid | solid | solid | solid | solid | solid |
| Melting point of oil phase | — | — | | | | | | | |
| Water phase (40%) | | | | | | | | | |
| purified water | 10 | 10 | 10 | 10 | 10 | 10 | 10 | 10 | 10 |
| polyethylene glycol 6000 | 30 | 30 | 30 | 30 | 30 | 30 | 30 | 30 | 30 |
| Properties of oil phase | solid | solid | solid | solid | solid | solid | solid | solid | solid |
| Properties of the products | liquid | liquid | semi-solid | solid | solid | solid | solid | solid | solid |
| Stability | x | x | ○ | ○ | ○ | ○ | ○ | ○ | ○ |

TABLE 2

| | Test examples | | | | | | | | |
|---|---|---|---|---|---|---|---|---|---|
| | 1-10 | 1-11 | 1-12 | 1-13 | 1-14 | 1-15 | 1-16 | 1-17 | 1-18 |
| Oil phase (60%) | | | | | | | | | |
| liquid paraffin | 20 | 20 | 20 | 20 | 20 | 20 | 20 | 20 | 20 |
| microcrystalline wax | 40 | 40 | 40 | 40 | 40 | 40 | 40 | 40 | 40 |
| Properties of oil phase | solid | solid | solid | solid | solid | solid | solid | solid | solid |
| Water phase (40%) | | | | | | | | | |
| purified water | 40 | 30 | 20 | 15 | 10 | 5 | 3 | 1 | 0 |
| polyethylene glycol 6000 | 0 | 10 | 20 | 25 | 30 | 35 | 37 | 39 | 40 |
| Properties of water phase | liquid | liquid | liquid | semi-solid | solid | solid | solid | solid | solid |
| Properties of the products | liquid | semi-solid | semi-solid | solid | solid | solid | solid | solid | solid |
| Stability | x | x | x | ○ | ○ | ○ | ○ | ○ | ○ |

<Evaluation Standard>

TABLE 3

| | obtained | slightly obtained | not obtained |
|---|---|---|---|
| Stickiness | 0 | 1 | 2 |
| Unsuitability for the skin | 0 | 1 | 2 |
| Emollient effect | 2 | 1 | 0 |
| Persistence of emollient effect | 2 | 1 | 0 |

◯: representing evaluation point average of more than 1.5
Δ: representing evaluation point average between 0.5 and 1.5
X: representing evaluation point average of less than 0.5

TABLE 4

Examples 1-1 to 1-5 and Comparative examples 1-a to 1-d

| | Examples | | | | | | Comparative examples | | | |
|---|---|---|---|---|---|---|---|---|---|---|
| | 1-1 | 1-2 | 1-3 | 1-4 | 1-5 | 1-6 | 1-a | 1-b | 1-c | 1-d |
| Water phase | | | | | | | | | | |
| purified water | 5 | 10 | 5 | 10 | 5 | 10 | 30 | 45 | 3 | 7 |
| glycerin | 5 | 5 | — | 7 | — | 5 | 5 | 5 | — | 10 |
| 1,3-butylene glycol | — | 10 | 5 | — | — | 10 | — | 10 | — | 5 |
| polyethylene glycol 1500 | 25 | 20 | 5 | 10 | 5 | 20 | — | — | — | — |
| polyethylene glycol 6000 | 5 | 15 | — | 10 | 10 | 25 | 5 | — | 20 | — |
| polyethylene glycol 20000 | — | — | 5 | — | — | — | — | — | — | — |
| cellulose powder | — | — | — | 3 | — | — | — | — | — | — |
| Oil phase | | | | | | | | | | |
| liquid paraffin | 20 | 15 | 30 | — | 20 | 15 | 20 | 35 | 2 | 3 |
| squalane | — | — | — | 20 | — | — | — | — | — | — |
| dimethyl polysiloxane 5 cs | 5 | — | 10 | 5 | 20 | — | 35 | — | — | — |
| decamethyl cyclopentasiloxane | — | 5 | — | 15 | — | — | — | — | — | — |
| vaseline | 15 | 10 | 15 | 10 | 20 | — | 5 | — | 30 | 50 |
| microcrystalline wax | 20 | 10 | 20 | 10 | — | 10 | — | 5 | 45 | 25 |
| silicone powder | — | — | 5 | — | 20 | 5 | — | — | — | — |
| Stability | ◯ | ◯ | ◯ | ◯ | ◯ | Δ | X | X | ◯ | ◯ |
| Usability | | | | | | | | | | |
| emollient effect | ◯ | ◯ | ◯ | ◯ | ◯ | ◯ | ◯ | X | ◯ | ◯ |
| persistence of emollient effect | ◯ | ◯ | ◯ | ◯ | ◯ | ◯ | X | X | ◯ | Δ |
| thickness | ◯ | ◯ | ◯ | ◯ | ◯ | ◯ | Δ | X | ◯ | ◯ |
| stickiness | ◯ | ◯ | ◯ | ◯ | ◯ | ◯ | ◯ | ◯ | X | X |

As shown in Tables 3 and 4, the oil-water mixed composition containing a humectant-containing solid or semisolid oil phase, and a water phase which contains no surfactant has superior stability with passage of time and safety. This same composition also shows very little stickiness and sensation of unsuitability, has excellent emollient effect (i.e., to prevent the skin from dryness), and is persistent in preserving its emollient effect.

Embodiment 2

Adding a hydrophobic silica into solid or semisolid oil phase at room temperature.

In this embodiment, dimethyl silicated anhydrous silica or trimethyl silicated anhydrous silica are the most preferable hydrophobic silicas which gives rise to the highest stability with passage of time and usability.

Dimethyl silicated anhydrous silica, trimethyl silicated anhydrous silica and octyl silicated anhydrous silica can be obtained from NIHON AEROSIL Co.,Ltd. as AEROSIL R972, and R974, AEROSIL R812 and AEROSIL R805 respectively. Please note that this invention is not restricted to the use of only the three types of hydrophobic silica listed above.

In this embodiment, the hydrophobic silica is preferably made of 0.1 to 10% by weight and more preferably 0.5 to 5% by weight with respect to the whole amount of the oil-water mixed composition. If the amount of this component is less than 0.1% by weight, the oil-water mixed composition would be less stable at high temperature. If the amount of this component is more than 10% by weight, the oil-water mixed composition would be too rigid to use.

In addition to the hydrophobic silica, it is preferable to add a solid or semisolid oil component to make the oil phase solid or semisolid. This component is preferably made of 1 to 70% by weight and more preferably 5 to 40% by weight with respect to the whole amount of the oil-water mixed composition. If the amount of this component is less than 1% by weight, the oil-water mixed composition would be less stable at high temperature. If the amount of this component is more than 70% by weight, the oil-water mixed composition would be too rigid to use.

In this embodiment, as like Embodiment 1, it is also preferable to add humectants to the water phase. Preferably, the humectants is consisted of 1 to 70% by weight and more preferably 5 to 40% by weight with respect to the whole amount of the oil-water mixed composition. If the humectants is less than 1% by weight, the composition would be less stable at high temperature. If the humectants constitute more than 70% by weight, the composition would become too sticky and less useful.

The humectants used in this embodiment are not restricted to the solid or semisolid ones. Examples of the humectants include polyethylene glycol, propylene glycol, dipropylene glycol, 1,3-butylene glycol, glycerin, diglycerine, sorbitol, maltitol, mucopolysaccharide, hyaluronic acid, chondroitin sulfate, erythritol, trimethyl glycin, lactic acid, sodium lactate, sodium pyrrolidonecarboxylate, and the like. 1,3-butylene glycol and glycerin are the most preferable ones in view of the effect.

The results of this embodiments are shown as follows.

The methods of test and evaluation are used in this embodiment are the same as those in embodiment 1.

TABLE 5

|  | Test examples | | | | | | | | |
| --- | --- | --- | --- | --- | --- | --- | --- | --- | --- |
|  | 2-1 | 2-2 | 2-3 | 2-4 | 2-5 | 2-6 | 2-7 | 2-8 | 2-9 |
| Oil phase (60%) | | | | | | | | | |
| liquid paraffin | 55 | 45 | 35 | 25 | 15 | 10 | 5 | 1 | 0 |
| microcrystalline wax | 0 | 10 | 20 | 30 | 40 | 45 | 50 | 54 | 55 |
| dimethyl silicated anhydrous silica | 5 | 5 | 5 | 5 | 5 | 5 | 5 | 5 | 5 |
| Properties of oil phase | liquid | liquid | liquid | semi-solid | solid | solid | solid | solid | solid |
| Melting point of oil phase | — | — | — | | | | | | |
| Water phase (40%) | | | | | | | | | |
| purified water | 30 | 30 | 30 | 30 | 30 | 30 | 30 | 30 | 30 |
| glycerin | 10 | 10 | 10 | 10 | 10 | 10 | 10 | 10 | 10 |
| Properties of oil phase | liquid | liquid | liquid | liquid | liquid | liquid | liquid | liquid | liquid |
| Properties of the products | liquid | liquid | semi-solid | semi-solid | solid | solid | solid | solid | solid |
| Stability | x | x | x | ○ | ○ | ○ | ○ | ○ | ○ |

TABLE 6

|  | Test examples | | | | | | | | |
| --- | --- | --- | --- | --- | --- | --- | --- | --- | --- |
|  | 2-10 | 2-11 | 2-12 | 2-13 | 2-14 | 2-15 | 2-16 | 2-17 | 2-18 |
| Oil phase (60%) | | | | | | | | | |
| liquid paraffin | 20 | 19.9 | 19.5 | 19 | 17 | 15 | 13 | 10 | 5 |
| microcrystalline wax | 40 | 40 | 40 | 40 | 40 | 40 | 40 | 40 | 40 |
| dimethyl silicated anhydrous silica | 0 | 0.1 | 0.5 | 1 | 3 | 5 | 7 | 10 | 15 |
| Properties of oil phase | solid | solid | solid | solid | solid | solid | solid | solid | solid |
| Water phase (40%) | | | | | | | | | |
| purified water | 30 | 30 | 30 | 30 | 30 | 30 | 30 | 30 | 30 |
| glycerin | 10 | 10 | 10 | 10 | 10 | 10 | 10 | 10 | 10 |
| Properties of water phase | liquid | liquid | liquid | liquid | liquid | liquid | liquid | liquid | liquid |
| Properties of the products | semi-solid | semi-solid | solid | solid | solid | solid | solid | solid | solid |
| Stability | x | Δ | ○ | ○ | ○ | ○ | ○ | ○ | ○ |
| Feel of use with a view of hardness | — | ○ | ○ | ○ | ○ | ○ | Δ | Δ | x |

As shown in Table 5, when the oil phase is in liquid form the oil-water mixed composition is less stable, even if hydrophobic silica is added to the oil phase. However, when the oil phase is semisolid or solid and contains hydrophobic silica, the stability of the oil-water mixed composition is much improved, even if its water phase is liquid form.

As demonstrated in Table 6, when as little as 0.1% by weight of hydrophobic silica is added to the oil phase, the stability of the oil-water mixed composition can be greatly improved. And, the remarkable stability of the composition can be reached when 0.5% by weight of hydrophobic silica is added. However, when more than 5% by weight of hydrophobic silica is added to the oil phase, the composition starts to get hard. When the amount of hydrophobic silica reaches 10% by weight, the composition starts to become unsuitable for skin use.

As a result of foregoing, the stability of the oil-water mixed composition can be greatly improved if hydrophobic silica is added to the oil phase and set it semisolid or solid.

The inventors also have manufactured the various oil-water mixed composition and studied the stability and the usability of these compositions.

TABLE 7

Examples 2-1 to 2-6 and Comparative examples 2-a to 2-d

|  | Examples | | | | | | Comparative examples | | | |
|---|---|---|---|---|---|---|---|---|---|---|
|  | 2-1 | 2-2 | 2-3 | 2-4 | 2-5 | 2-6 | 2-a | 2-b | 2-c | 2-d |
| Water phase | | | | | | | | | | |
| purified water | 5 | 40 | 20 | 10 | 5 | 5 | 50 | 21 | 3 | 40 |
| glycerin | 10 | 5 | — | 5 | — | 5 | 5 | 3 | — | 5 |
| 1,3-butylene glycol | — | — | 10 | 5 | — | — | — | — | — | 5 |
| polyethylene glycol 1500 | 15 | 10 | 20 | — | 20 | 30 | 5 | — | — | 10 |
| polyethylene glycol 6000 | 10 | 5 | — | — | 15 | 10 | — | — | — | 5 |
| polyethylene glycol 20000 | — | — | 5 | — | — | — | — | — | 20 | — |
| silk powder | — | — | 5 | — | — | — | — | — | — | — |
| Oil phase | | | | | | | | | | |
| liquid paraffin | 15 | 20 | 18 | — | 15 | 40 | 20 | 52 | 2 | 20 |
| squalane | — | — | — | 19 | — | — | — | — | — | — |
| dimethylpolysiloxane 5 cs | — | — | — | 5 | — | — | — | — | — | — |
| decamethyl cyclopentasiloxane | 32 | 16 | — | 20 | 27 | — | 20 | 24 | — | 15 |
| dimethyl silicated anhydrous silica | 3 | 4 | 2 | 3 | 3 | 5 | — | — | — | — |
| vaseline | 5 | — | 10 | 15 | 10 | — | — | — | 30 | — |
| microcrystalline wax | 5 | — | 10 | 15 | 5 | 1 | — | — | 45 | 5 |
| silicone powder | — | — | — | 3 | — | 4 | — | — | — | — |
| Stability | ○ | ○ | ○ | ○ | ○ | ○ | x | x | ○ | x |
| Usability | ○ | ○ | ○ | ○ | ○ | ○ | Δ | x | ○ | x |
| emollient effect | | | | | | | | | | |
| persistence of emollient effect | ○ | ○ | ○ | ○ | ○ | ○ | x | x | ○ | x |
| thickness | ○ | ○ | ○ | ○ | ○ | ○ | Δ | x | ○ | x |
| stickiness | ○ | ○ | ○ | ○ | ○ | ○ | ○ | ○ | x | Δ |

As shown from foregoing, the oil-water mixed composition which is consisted of a hydrophobic silica containing solid or semisolid oil phase, and a water phase that has no surfactant has superior stability with passage of time and safety. This same composition also shows very little stickiness and sensation of unsuitability, has excellent emollient effect (i.e., to prevent the skin from dryness), and is persistent in preserving its emollient effect.

Embodiment 3

Adding a dextrin fatty acid ester into the solid or semisolid oil phase at room temperature.

The dextrin fatty acid ester used in this embodiment is formed by esterifying dextrin with a fatty acid that have a carbon number between 12 and 22. Examples of these dextrin fatty acid esters include dextrin laurate, dextrin myristate, dextrin stearate, dextrin behenete, dextrin cocoate and the like. Among these dextrin fatty acid esters, dextrin palmitate is the most preferable in terms of producing superior stability and usability in the oil-water mixed composition.

Please note that although most of the dextrin fatty acid esters that we have tested in this embodiment are obtained from CHIBA FLOUR MILLING Co.,Ltd. as REOPEARL KL, REOPEARL KE and the like, this invention is not restricted to only those listed above.

In this embodiment, the amount of dextrin fatty acid ester that is added to the oil phase is preferably 0.1 to 10% by weight and more preferably 0.5 to 7% by weight with respect to the whole amount of the oil-water mixed composition. If the amount of dextrin fatty acid ester is less than 0.1% by weight, the composition is unstable at high temperature. If the amount of dextrin fatty acid ester exceeds 10% by weight, the composition becomes too sticky to use.

In this embodiment, though a solid oil component which set oil phase solid or semisolid is same as embodiment 1, this oil component is preferably compounded with 1 to 70% by weight and more preferably 5 to 40% by weight with respect to the whole amount of the oil-water mixed composition. If the amount of the oil component is less than 1% by weight, the composition is unstable at high temperature. However, if the amount of the oil component exceeds 70% by weight, the composition would be too rigid to use.

In this embodiment, it is also preferable to add a humectant into the water phase of the oil-water mixed composition. The preferable amount of the humectant added is in the range of 1 to 70% by weight, and is more preferably between 5 and 40% by weight, with respect to the whole amount of the oil-water mixed composition. If the amount of humectant is less than 1% by weight, the composition is not stable at high temperature. On the other hand, if the amount of exceeds 70% by weight, the composition becomes too sticky to use.

The kinds of the humectants used in this embodiment are the same as those in embodiment 2.

Next, it will be explained the test results of this embodiment.

The method of test and evaluation used in this embodiment is the same as that used in embodiment 1.

TABLE 8

|  | Test examples | | | | | | | | |
|---|---|---|---|---|---|---|---|---|---|
|  | 3-1 | 3-2 | 3-3 | 3-4 | 3-5 | 3-6 | 3-7 | 3-8 | 3-9 |
| Oil phase (60%) | | | | | | | | | |
| liquid paraffin | 55 | 45 | 35 | 25 | 15 | 10 | 5 | 1 | 0 |
| microcrystalline wax | 0 | 10 | 20 | 30 | 40 | 45. | 50 | 54 | 55 |
| dextrin palmitate | 5 | 5 | 5 | 5 | 5 | 5 | 5 | 5 | 5 |
| Properties of oil phase | liquid | liquid | liquid | semi-solid | solid | solid | solid | solid | solid |
| Melting point of oil phase | — | — | — | | | | | | |

TABLE 8-continued

|  | Test examples | | | | | | | | |
|---|---|---|---|---|---|---|---|---|---|
|  | 3-1 | 3-2 | 3-3 | 3-4 | 3-5 | 3-6 | 3-7 | 3-8 | 3-9 |
| Water phase (40%) | | | | | | | | | |
| purified water | 30 | 30 | 30 | 30 | 30 | 30 | 30 | 30 | 30 |
| glycerin | 10 | 10 | 10 | 10 | 10 | 10 | 10 | 10 | 10 |
| Properties of oil phase | liquid | liquid | liquid | liquid | liquid | liquid | liquid | liquid | liquid |
| Properties of the products | liquid | liquid | liquid | semi-solid | solid | solid | solid | solid | solid |
| stability | x | x | x | ○ | ○ | ○ | ○ | ○ | ○ |

TABLE 9

|  | Test examples | | | | | | | | |
|---|---|---|---|---|---|---|---|---|---|
|  | 3-10 | 3-11 | 3-12 | 3-13 | 3-14 | 3-15 | 3-16 | 3-17 | 3-18 |
| Oil phase (60%) | | | | | | | | | |
| liquid paraffin | 20 | 19.9 | 19.5 | 19 | 17 | 15 | 13 | 10 | 5 |
| microcrystalline wax | 40 | 40 | 40 | 40 | 40 | 40 | 40 | 40 | 40 |
| dextrin palmitate | 0 | 0.1 | 0.5 | 1 | 3 | 5 | 7 | 10 | 15 |
| Properties | solid | solid | solid | solid | solid | solid | solid | solid | solid |
| water phase (40%) | | | | | | | | | |
| purified water | 30 | 30 | 30 | 30 | 30 | 30 | 30 | 30 | 30 |
| glycerin | 10 | 10 | 10 | 10 | 10 | 10 | 10 | 10 | 10 |
| Properties of water phase | liquid | liquid | liquid | liquid | liquid | liquid | liquid | liquid | liquid |
| Properties of the products | semi-solid | semi-solid | solid | solid | solid | solid | solid | solid | solid |
| Stability | x | Δ | ○ | ○ | ○ | ○ | ○ | ○ | ○ |
| Feel of use with a view of stickiness | — | ○ | ○ | ○ | ○ | ○ | Δ | Δ | x |

As demonstrated in Table 8, the oil-water mixed composition is less stable when its oil phase is in liquid form, even if dextrin fatty acid ester has been added to the oil phase. However, when the oil phase is semisolid or solid and contains dextrin fatty acid ester, the stability of the composition is greatly improved even if the water phase of the composition is in liquid form.

On the other hand, as shown in Table 9, when 0.1% of dextrin fatty acid ester is added to the oil phase, the stability of the oil-water mixed composition is improved. The stability of the oil-water mixed composition is much improved when 0.5% by weight of dextrin fatty acid ester is added to the oil phase, and begins to harden when 5% by weight of dextrin fatty acid ester is added. In the case where more than 10% by weight of dextrin fatty acid ester is added to the oil phase, the sensation of use is worsened.

As a results of the foregoing, it was observed excellent stability when dextrin fatty acid ester is contained in the oil phase of the oil-water mixed composition and set it semi-solid and solid.

The inventors also have manufactured the various oil-water mixed composition and studied the stability and the usability of these compositions.

TABLE 10

Examples 3-1 to 3-8 and Comparative examples 3-a to 2-d

|  | Examples | | | | | | | | Comparative examples | | | |
|---|---|---|---|---|---|---|---|---|---|---|---|---|
|  | 3-1 | 3-2 | 3-3 | 3-4 | 3-5 | 3-6 | 3-7 | 3-8 | 3-a | 3-b | 3-c | 3-d |
| Water phase | | | | | | | | | | | | |
| purified water | 35 | 10 | 5 | 15 | 10 | 10 | 25 | 5 | 50 | 21 | 2 | 35 |
| glycerin | 5 | 5 | — | 10 | 3 | 5 | 10 | 5 | 5 | 3 | — | 35 |
| 1,3-butylene glycol | 5 | — | 10 | 5 | — | — | 5 | — | — | — | — | 5 |
| polyethylene glycol 1500 | 5 | 5 | 15 | 20 | — | 5 | — | 40 | — | — | — | 5 |
| polyethylene glycol 6000 | 10 | — | — | — | — | — | — | 4 | 5 | — | — | 5 |
| polyethylene glycol 20000 | — | — | 10 | 5 | 2 | — | — | — | — | — | 20 | — |
| mica | — | — | — | 5 | — | — | — | — | — | — | — | — |
| Oil phase | | | | | | | | | | | | |
| liquid paraffin | 18 | 20 | 19 | — | 20 | 20 | 10 | 30 | 20 | 52 | 3 | 20 |
| squalane | — | — | — | 20 | — | — | — | 10 | — | — | — | — |
| dimethyl-polysiloxane 5 cs | — | — | 10 | 5 | — | — | 5 | — | 20 | — | — | — |
| decamethyl cyclopenta-siloxane | 5 | 26 | — | — | 16 | 26 | 25 | — | — | 24 | — | 5 |
| dextrin palmitate | 2 | 4 | 3 | 2 | 4 | — | 5 | 5 | — | — | — | — |
| dextrin stearate | — | — | — | — | — | 4 | — | — | — | — | — | — |

TABLE 10-continued

Examples 3-1 to 3-8 and Comparative examples 3-a to 2-d

|  | Examples | | | | | | | | Comparative examples | | | |
| --- | --- | --- | --- | --- | --- | --- | --- | --- | --- | --- | --- | --- |
|  | 3-1 | 3-2 | 3-3 | 3-4 | 3-5 | 3-6 | 3-7 | 3-8 | 3-a | 3-b | 3-c | 3-d |
| vaseline | 5 | 15 | 15 | 5 | 25 | 15 | 5 | — | — | — | 40 | 5 |
| paraffin wax | 10 | 15 | 10 | 5 | 20 | 15 | 10 | 1 | — | — | 35 | 10 |
| talc | — | — | 3 | — | — | — | — | — | — | — | — | — |
| jojoba oil | — | — | — | 3 | — | — | — | — | — | — | — | — |
| Stability | o | o | o | o | o | o | o | o | x | x | o | x |
| Usability stickiness | o | o | o | o | Δ | o | o | o | o | o | x | Δ |
| unsuitable for skin | o | o | o | o | o | o | o | o | Δ | Δ | x | Δ |
| emollient effect | o | o | o | o | o | o | o | o | Δ | x | o | Δ |
| persistence of emollient effect | o | o | o | o | o | o | o | o | x | x | o | x |

As shown from foregoing, the oil-water mixed composition which is consisted of a dextrin fatty acid containing solid or semisolid oil phase, and a water phase that has no surfactant has superior stability with passage of time and safety. This composition also shows very little stickiness and sensation of unsuitability, has excellent emollient effect (i.e., to prevent the skin from dryness), and is persistent in preserving its emollient effect.

Embodiment 4

Adding a polyvalent alcohol oligo esters consisting of long chain monocarboxylic acid and long chain dicarboxylic acid. The polyvalent alcohol oligo esters are derived from esterification of polyvalent alcohol with monocarboxylic acid and dicarboxylic acid having a carbon number of 12 to 22, respectively. This composition is further contained more than one polyvalent alcohol.

Examples of the polyvalent alcohol used for manufacturing this compounding include glycerin, glycerin condensate, trimethylolethane, trimethylolpropane, pentaerythritol and the like.

Examples of monocarboxylic acid having a carbon number 12 to 22 include straight chain fatty acid, branched chain fatty acid, unsaturated fatty acid, hydroxy fatty acid and the like having a carbon number 12 to 22. Lauric acid, myristic acid, stearic acid, behenic acid, 2-ethylhexanoic acid, neotridecanoic acid, isostearic acid, oleic acid, 12-hydroxystearic acid and the like are corresponded to those ingredients.

Examples of dicarboxylic acid having a carbon number 12 to 22 are dibasic acid which has straight chain or branched chain having a carbon number 12 to 22. Dodecandicarboxylic acid, tetradecandicarboxylic acid, hexadecandicarboxylic acid, octadecandicarboxylic acid, eicosandi carboxylic acid, 7-ethyl octadecandi carboxylic acid and the like are corresponded to those ingredients.

Please note that although the preparations of most of the above polyvalent alcohol oligo ester has been disclosed in a Japanese Patent Publication No.61-7403, one particular polyvalent alcohol oligo ester, i.e., glycerin behenate eicosan dicarboxylic oligo ester, which has shown superior stability and usability when added to the oil-water mixes composition, is not disclosed in the above named patent.

In this embodiment, the amount of polyvalent alcohol oligo ester that is added to the oil phase of the oil-water mixed composition is preferably in the range of 0.1 to 10% by weight and more preferably 0.5 to 5% with respect to the whole amount of the oil-water mixed composition. If the amount of polyvalent oligo ester is below 0.1% by weight, the composition is unstable at high temperature. If more than 10% by weight of polyvalent alcohol oligo ester is added to the oil phase, the composition becomes too sticky to use.

It is preferable to add a solid or semisolid oil component which can set the oil phase solid or semisolid, in the amount of 1 to 70% by weight, or more preferably in the amount of 5 to 40% by weight, to the oil phase of the oil-water mixed composition. If the amount of the oil component is below 1% by weight, the oil-water mixed composition is unstable at high temperature. If the amount of the oil component exceeds 70% by weight, the oil-water mixed composition becomes too rigid to use.

In this embodiment, it is also preferable to add the humectant to the water phase as like embodiment 2 or 3. In this case, the amount of the humectant that is added to the water phase of the oil-water mixed composition is preferably in the range of 1 to 70% by weight and more preferably 5 to 40% by weight with respect to the whole amount of the oil-water mixed composition. If the amount of the humectant is less than 1% by weight, the composition is not stable at high temperature. If more than 70% by weight of humectant is added to the water phase, the composition becomes too sticky to use.

Next, it will be explained the test results of this embodiment.

The method of test and evaluation are the same as embodiment 1.

TABLE 11

|  | Test examples | | | | | | | | |
| --- | --- | --- | --- | --- | --- | --- | --- | --- | --- |
|  | 4-1 | 4-2 | 4-3 | 4-4 | 4-5 | 4-6 | *4-7 | 4-8 | 4-9 |
| Oil phase (60%) | | | | | | | | | |
| liquid paraffin | 55 | 45 | 35 | 25 | 15 | 10 | 5 | 1 | 0 |
| microcrystalline wax | 0 | 10 | 20 | 30 | 40 | 45 | 50 | 54 | 55 |
| glycerin behenate eicosan dicarboxylic ester | 5 | 5 | 5 | 5 | 5 | 5 | 5 | 5 | 5 |
| Properties of oil phase | liquid | liquid | liquid | semi-solid | solid | solid | solid | solid | solid |
| Water phase (40%) | | | | | | | | | |
| purified water | 30 | 30 | 30 | 30 | 30 | 30 | 30 | 30 | 30 |
| glycerin | 10 | 10 | 10 | 10 | 10 | 10 | 10 | 10 | 10 |

TABLE 11-continued

|  | Test examples | | | | | | | | |
|---|---|---|---|---|---|---|---|---|---|
|  | 4-1 | 4-2 | 4-3 | 4-4 | 4-5 | 4-6 | *4-7 | 4-8 | 4-9 |
| Properties of water phase | liquid | liquid | liquid | liquid | liquid | liquid | liquid | liquid | liquid |
| Properties of the products | liquid | liquid | liquid | semi-solid | solid | solid | solid | solid | solid |
| Stability | x | x | x | ○ | ○ | ○ | ○ | ○ | ○ |

TABLE 12

|  | Test examples | | | | | | | | |
|---|---|---|---|---|---|---|---|---|---|
|  | 4-10 | 4-11 | 4-12 | 4-13 | 4-14 | 4-15 | 4-16 | 4-17 | 4-18 |
| Oil phase (60%) | | | | | | | | | |
| liquid paraffin | 20 | 19.9 | 19.5 | 19 | 17 | 15 | 13 | 10 | 5 |
| microcrystalline wax | 40 | 40 | 40 | 40 | 40 | 40 | 40 | 40 | 40 |
| glycerin behenate eicosan dicarboxylic ester | 0 | 0.1 | 0.5 | 1 | 3 | 5 | 7 | 10 | 15 |
| Properties of oil phase | solid | solid | solid | solid | solid | solid | solid | solid | solid |
| Water phase (40%) | | | | | | | | | |
| purified water | 30 | 30 | 30 | 30 | 30 | 30 | 30 | 30 | 30 |
| glycerin | 10 | 10 | 10 | 10 | 1Q | 10 | 10 | 10 | 10 |
| Properties of water phase | liquid | liquid | liquid | liquid | liquid | liquid | liquid | liquid | liquid |
| Properties of the products | liquid | solid | solid | solid | solid | solid | solid | solid | solid |
| Stability | x | Δ | ○ | ○ | ○ | ○ | ○ | ○ | ○ |
| Feel of use with a view of stickiness | — | ○ | ○ | ○ | ○ | ○ | Δ | Δ | x |

As shown in Table 1, when the oil phase is in liquid form, the oil-water mixed composition is much less stable, even if polyvalent alcohol oligo ester has been added to the oil phase. However, when the oil phase is semisolid or solid, the addition of polyvalent oligo ester would remarkably improved the stability of the oil-water mixed composition, even if the water phase of the composition is in liquid form.

On the other hand, as shown in Table 2, when as little as 0.1% by weight polyvalent alcohol oligo ester is added to the oil phase, the stability of the oil-water mixed composition is improved. And the remarkable stability of the composition can be reached when 0.5% by weight of polyvalent alcohol oligoester is added. However, when more than 5% by weight of polyvalent alcohol oligo ester is added, the composition becomes too rigid to use. When more than 10% by weight of polyvalent alcohol oligo ester is added, the sensation of use is worsened.

The above results suggest that the addition of polyvalent alcohol oligo ester to an oil phase and set it semisolid or solid, can remarkably improve the stability of the oil-water mixed composition.

Next, the inventors have also manufactured the various oil-water mixed composition and studied the stability and the usability of these compositions.

TABLE 13

Examples 4-1 to 4-8 and Comparative examples 4-a to 4-d

|  | Examples | | | | | | | | Comparative examples | | | |
|---|---|---|---|---|---|---|---|---|---|---|---|---|
|  | 4-1 | 4-2 | 4-3 | 4-4 | 4-5 | 4-6 | 4-7 | 4-8 | 4-a | 4-b | 4-c | 4-d |
| Water phase | | | | | | | | | | | | |
| purified water | 35 | 15 | 20 | 45 | 15 | 15 | 25 | 5 | 50 | 21 | 3 | 15 |
| glycerin | 5 | 3 | — | 5 | 3 | 3 | 10 | — | 5 | 3 | — | 3 |
| 1,3-butylene glycol | 15 | — | 10 | 5 | — | — | 5 | 5 | — | — | — | — |
| polyethylene glycol 1500 | 5 | 2 | 10 | — | 2 | 2 | — | 40 | 5 | — | 20 | 2 |
| iron oxide (black) | — | — | — | 5 | — | — | — | — | — | — | — | — |

TABLE 13-continued

Examples 4-1 to 4-8 and Comparative examples 4-a to 4-d

| | Examples | | | | | | | | Comparative examples | | | |
|---|---|---|---|---|---|---|---|---|---|---|---|---|
| | 4-1 | 4-2 | 4-3 | 4-4 | 4-5 | 4-6 | 4-7 | 4-8 | 4-a | 4-b | 4-c | 4-d |
| Oil phase | | | | | | | | | | | | |
| liquid paraffin | 18 | 26 | 19 | — | 20 | 26 | 10 | 30 | 20 | 52 | 2 | 26 |
| macadamia-nuts oil | — | — | — | 5 | — | — | — | 10 | — | — | — | 4 |
| dimethyl polysiloxane 5 cs | — | — | 10 | 23 | — | — | 5 | — | — | — | — | — |
| decamethylcyclopentasiloxane | 5 | 20 | 15 | — | 10 | 20 | 25 | — | 20 | 24 | — | 20 |
| glycerin behenate eicosan dicarboxylic ester | 2 | 4 | 3 | 2 | 6 | — | 5 | 5 | — | — | — | — |
| trimethylol ethane stearate eicosan dicarboxylic ester | — | — | — | — | 4 | — | — | — | — | — | — | — |
| vaseline | 5 | 15 | — | 5 | 20 | 15 | 10 | — | — | — | 30 | 15 |
| paraffin wax | 10 | 15 | 10 | 5 | 20 | 15 | 5 | 1 | — | — | 45 | 10 |
| silicone-coated titanium dioxide | — | — | 3 | — | — | — | — | 4 | — | — | — | — |
| Stability | o | o | o | o | o | o | o | o | x | x | o | x |
| Usability | | | | | | | | | | | | |
| stickiness | o | o | o | o | Δ | Δ | o | o | o | o | x | Δ |
| unsuitable for skin use | o | o | o | o | o | o | o | o | Δ | x | x | Δ |
| emollient effect | o | o | o | o | o | o | o | o | Δ | x | o | Δ |
| persistence of emollient effect | o | o | o | o | o | o | o | o | x | x | o | x |

As shown from foregoing, the oil-water mixed composition which is consisted of a polyvalent alcohol oligo ester-containing solid or semisolid oil phase, and a water phase that has no surfactant has superior stability with passage of time and safety. This composition also is superior in usability, i.e., with little or no stickiness and unsuitability, having high emollient effect (i.e., to prevent the skin from dryness) and persistent in preserving its emollient effect.

We claim:

1. An oil-water mixed composition consisting of:
    an oil phase, said oil phase comprising an oil component which makes said oil phase a solid or semisolid at room temperature, wherein said oil component is selected from the group consisting of microcrystalline wax, solid paraffin, hydrogenated oil, tallow, Japan wax, beeswax, candelilla wax, carnauba wax, ceresin, vaseline, lanolin, lanolin derivative, cholesterol, and cholesterol ester; and
    a water phase dispersed into said oil phase, wherein said water phase comprises a humectant which makes said water phase solid or semisolid at room temperature, wherein said humectant is in the range of more than 10% and no more than 70% by weight of the whole amount of said composition,
    wherein said composition does not contain a surfactant.

2. An oil-water mixed composition according to claim 1, wherein said oil component constitutes 10 to 70% by weight with respect to the whole amount of said composition.

3. An oil-water mixed composition according to claim 1, wherein said oil component is microcrystalline wax or vaseline.

4. An oil-water mixed composition according to claim 1, wherein said humectant is selected from the group consisting of polyethylene glycol, sorbitol, maltitol, hyaluronic acid, chondroitin sulfate, erythritol, trimethyl glycin, sodium lactate, and pyrrolidonecarboxylic acid.

5. An oil-water mixed composition according to claim 1, wherein said humectant is polyethylene glycol.

6. An oil-water mixed composition according to claim 1, wherein said humectant is selected from the group consisting of polyethylene glycol, propylene glycol, dipropylene glycol, 1,3-butylene glycol, glycerin, diglycerine, sorbitol, maltitol, mucopolysaccharide, hyaluronic acid, chondroitin sulfate, erythritol, trimethyl glycin, lactic acid, sodium lactate, and sodium pyrrolidonecarboxylic acid.

7. An oil-water mixed composition according to claim 1, wherein said humectant is 1,3-butylene glycol or glycerin.

8. An oil-water mixed composition consisting of:
    an oil phase, wherein said oil phase comprises an oil component and a hydrophobic silica to make said oil phase solid or semisolid at room temperature, wherein said oil component is selected from the group consisting of microcrystalline wax, solid paraffin, hydrogenated oil, tallow, Japan wax, beeswax, candelilla wax, carnauba wax, ceresin, vaseline, lanolin, lanolin derivative, cholesterol, and cholesterol ester; and
    a water phase dispersed into said oil phase, wherein said composition does not contain a surfactant.

9. An oil-water mixed composition according to claim 8, wherein said oil phase forms a continuous phase.

10. An oil-water mixed composition according to claim 8, wherein said hydrophobic silica constitutes 0.1 to 10% by weight with respect to the whole amount of said composition.

11. An oil-water mixed composition according to claim 8, wherein said oil component constitutes 1 to 70% by weight with respect to the whole amount of the composition.

12. An oil-water mixed composition according to claim 8, wherein said water phase contains a humectant and said humectants constitutes 1–70% by weight with respect to the whole amount of the composition.

13. An oil-water mixed composition consisting of:
an oil phase, wherein said oil phase comprises an oil component and a dextrin fatty acid to make said oil phase solid or semisolid at room temperature, wherein said oil component is selected from the group consisting of microcrystalline wax, solid paraffin, hydrogenated oil, tallow, Japan wax, beeswax, candelilla wax, carnauba wax, ceresin, vaseline, lanolin, lanolin derivative, cholesterol, and cholesterol ester; and
a water phase dispersed into said oil phase,
wherein said composition does not contain a surfactant.

14. An oil-water mixed composition according to claim 13, wherein said oil phase forms a continuous phase.

15. An oil-water mixed composition according to claim 13, wherein said dextrin fatty acid ester constitutes 0.1 to 10% by weight with respect to the whole amount of said composition.

16. An oil-water mixed composition according to claim 13, wherein said oil component constitutes 1 to 70% by weight with respect to the whole amount of said composition.

17. An oil-water mixed composition according to claim 13, wherein said water phase contains a humectant and said humectant constitutes 1 to 70% by weight with respect to the whole amount of said composition.

18. An oil-water mixed composition according to claim 13, said dextrin fatty acid ester having a fatty acid with carbon number between 12 and 22.

19. An oil-water mixed composition according to claim 13, wherein said dextrin fatty acid ester is selected from the group consisting of dextrin laurate, dextrin myristate, dextrin stearate, dextrin behenate, and dextrin cocoate.

20. An oil-water mixed composition according to claim 13, wherein said dextrin fatty acid ester is dextrin palmitate.

21. An oil-water mixed composition consisting of:
an oil phase, wherein said oil phase comprises an oil component and a polyvalent alcohol oligo ester, wherein said oil component is selected from the group consisting of microcrystalline wax, solid paraffin, hydrogenated oil, tallow, Japan wax, beeswax, candelilla wax, carnauba wax, ceresin, vaseline, lanolin, lanolin derivative, cholesterol, and cholesterol ester; and
a water phase dispersed into said oil phase,
wherein said composition does not contain a surfactant.

22. An oil-water mixed composition according to claim 21, wherein said oil phase forms a continuous phase.

23. An oil-water mixed composition according to claim 21, wherein said polyvalent alcohol oligo ester comprises:
(a) a polyvalent alcohol, wherein said polyvalent alcohol is selected from the group consisting of glycerin, glycerin condensate, trimethylolethane, trimethylolpropane, and pentaerythritol;
(b) a monocarboxylic acid having a carbon number of 12 to 22, wherein said monocarboxylic acid is selected from the group consisting of straight chain fatty acid, branched chain fatty acid, and hydroxy fatty acid; and
(c) a dicarboxylic acid having a carbon number of 12 to 22, wherein said dicarboxylic acid is straight or branched dibasic acid.

24. An oil-water mixed composition according to claim 23, wherein said polyvalent alcohol oligo ester is glycerin behenate eicosandicarboxylic ester.

25. An oil-water mixed composition according to claim 21, wherein said polyvalent alcohol oligo ester constitutes 0.1 to 10% by weight with respect to the whole amount of said composition.

26. An oil-water mixed composition according to claim 21, wherein said oil component constitutes 1 to 70% by weight with respect to the whole amount of said composition.

27. An oil-water mixed composition according to claim 21, wherein said water phase contains a humectant and said humectants constitutes 1 to 70% by weight with respect to the whole amount of said composition.

* * * * *